US012623009B2

(12) United States Patent
Yuds et al.

(10) Patent No.: US 12,623,009 B2
(45) Date of Patent: May 12, 2026

(54) REDUCING BIOFILM BUILD-UP IN A DIALYSATE PATHWAY BY USING ULTRASONICATION AND IONIZATION

(71) Applicants: Fresenius Medical Care Holdings, Inc., Waltham, MA (US); Fresenius Medical Care Deutschland GmbH, Bad Homburg (DE)

(72) Inventors: David Yuds, Hudson, NH (US); Martin Crnkovich, Walnut Creek, CA (US); Christian Schlaeper, Wehrheim (DE)

(73) Assignees: FRESENIUS MEDICAL CARE HOLDINGS, INC., Waltham, MA (US); FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 61 days.

(21) Appl. No.: 18/768,768

(22) Filed: Jul. 10, 2024

(65) Prior Publication Data

US 2025/0041495 A1     Feb. 6, 2025

Related U.S. Application Data

(60) Provisional application No. 63/530,105, filed on Aug. 1, 2023.

(51) Int. Cl.
*A61M 1/16*        (2006.01)
*B08B 7/02*        (2006.01)
(Continued)

(52) U.S. Cl.
CPC ............. *A61M 1/169* (2013.01); *B08B 7/028* (2013.01); *B08B 7/04* (2013.01); *B08B 9/0325* (2013.01);
(Continued)

(58) Field of Classification Search
None
See application file for complete search history.

(56) References Cited

U.S. PATENT DOCUMENTS

| | | | |
|---|---|---|---|
| 6,027,572 A | 2/2000 | Labib et al. | |
| 11,690,942 B2 * | 7/2023 | Ichikawa ............ | A61M 1/1629 |
| | | | 210/96.2 |

(Continued)

FOREIGN PATENT DOCUMENTS

| | | |
|---|---|---|
| AU | 2019101517 A4 | 3/2020 |
| CN | 1235849 A | 11/1999 |

(Continued)

OTHER PUBLICATIONS

International Search Report for PCT/US2024/037332 dated Oct. 21, 2024, issued by the KIPO as ISA 5 pages.

(Continued)

*Primary Examiner* — Eric W Golightly
(74) *Attorney, Agent, or Firm* — Kilyk & Bowersox, P.L.L.C.

(57)        ABSTRACT

A hydraulic system and method are provided for breaking-up, dislodging, removing, and preventing the build-up of biofilm in a dialysate pathway of an extracorporeal blood treatment device. The dialysate pathway can include a dialyzer discharge line, a drain line, a dialyzer feed line, and a bypass system. At least one ultrasonic device can be positioned and configured to generate ultrasonic waves in the dialysate pathway and to propagate the ultrasonic waves along at least a portion of the dialysate pathway. The ultrasonic waves can be used to break-up biofilm. An ionizing electrode pair can also, or instead, be implemented to break-up, dislodge, remove, and prevent a build-up of biofilm. The system and method can particularly be imple- (Continued)

mented and useful in non-disposable portions of a hydraulic system of an extracorporeal blood treatment device.

20 Claims, 8 Drawing Sheets

(51) Int. Cl.
    *B08B 7/04*           (2006.01)
    *B08B 9/032*         (2006.01)

(52) U.S. Cl.
    CPC .... *A61M 2205/33* (2013.01); *B08B 2209/032*
                                       (2013.01)

(56) References Cited

U.S. PATENT DOCUMENTS

| | | | |
|---|---|---|---|
| 2002/0189647 | A1 | 12/2002 | Labib et al. |
| 2003/0222022 | A1 | 12/2003 | Connell et al. |
| 2005/0209563 | A1 | 9/2005 | Hopping et al. |
| 2011/0135534 | A1 | 6/2011 | Bates et al. |
| 2012/0271274 | A1 | 10/2012 | Reiter et al. |
| 2015/0283277 | A1 | 10/2015 | Schafer et al. |
| 2019/0358352 | A1 | 11/2019 | Qamar et al. |
| 2021/0015511 | A1 | 1/2021 | Behnke-Parls et al. |
| 2021/0346533 | A1 | 11/2021 | Cioanta et al. |
| 2022/0369628 | A1 | 11/2022 | McMahon et al. |

FOREIGN PATENT DOCUMENTS

| | | |
|---|---|---|
| CN | 110935075 A | 3/2020 |
| CN | 214865747 A | 11/2021 |
| CN | 114618036 A | 6/2022 |

OTHER PUBLICATIONS

Written Opinion of the ISA for PCT/US2024/037332 dated Oct. 21, 2024, issued by the KIPO 3 pages.

* cited by examiner

REDUCING BIOFILM BUILD-UP IN A DIALYSATE PATHWAY BY USING ULTRASONICATION AND IONIZATION

CROSS-REFERENCE TO RELATED APPLICATION

The present application claims the priority benefit of U.S. Provisional Patent Application No. 63/530,105, filed Aug. 1, 2023, which is incorporated herein in its entirety by reference.

BACKGROUND OF THE INVENTION

The present invention relates to reducing biofilm build-up in dialysis machines.

The hydraulic system of some hemodialysis machines, for example, the 2008T hemodialysis machine available from Fresenius USA, Inc. of Concord, California, generates dialysate using three streams: an acid stream, a bicarbonate stream, and a stream of purified water. After fresh dialysate is mixed, it is pumped by a balancing chamber through a dialyzer wherein toxins from counter-current-flowing blood pass through a semi-permeable membrane. The dialysate effluent is then pumped as spent dialysate from the dialyzer and through a complementary half of the balancing chamber. The spent dialysate then passes through a heat exchanger and is drained out of the machine.

Toxins and other organic matter pulled from the blood through the semi-permeable membrane and into the dialysate build up in the hydraulics of the machine over the course of the treatment and create biofilm. The hydraulics of the machine can include the entire dialysate side of the machine, that is, all of the plumbing and hydraulics involved with preparing fresh dialysate, draining spent dialysate, balancing fresh and spent dialysate, and circulating cleaning or sterilizing liquid through a dialysate pathway or dialysate circuit. Herein, a biofilm is defined as a collection of microorganisms (single or multiple species) that sticks to a surface. The biofilm can form a protective extracellular matrix or slime layer. The biofilm can attract other organisms and nutrients to enhance survival.

The effects of biofilms on dialysis machines and dialysis machine operation is described, for example, in the article of J. Maltais entitled *Biofilm, Where Does it Come From & Why is it Such a Problem*, NANT 33rd Annual National Symposium, Mar. 23, 2016, which is incorporated herein in its entirety by reference. The article can be accessed at the following webpage: https://www.dialysistech.net/images/NANT2016Presentations/BioFilm.pdf.

If the hydraulics of the machine are not properly disinfected, bacterial growth including in the form of biofilm can impede flow to the drain, damage components, corrode stainless steel, and lead to patient infections.

The initial adherence of a biofilm foundation, referred to as Stage 2, can occur in just twelve minutes under certain conditions. After that, the organic structure continues to be built by sending out signals to attract more bacteria to the safe haven in the dialysate flow path. A germ- and endo-toxin-free dialysate does not exclude the risks and hazards of bacteria and endotoxin discharge from biofilm developed in and on the fluid pathway tubing, chambers, and components. Biofilm can act as a reservoir for continuous contamination.

Mishandling acid concentrates and bicarbonate concentrates, or contamination of the reverse osmosis system upstream of a water inlet, can result in biofilm growth throughout dialysis machine hydraulics.

Practically all hydraulic systems for hemodialysis machines face the common problem of biofilm buildup. The industry response has always been chemical disinfection, heat disinfection, and replacing impacted components. In accordance with the report linked to https://www.ncbi.nlm-.nih.gov/pmc/articles/PMC5111172/sodium hypochlorite did not show good biofilm removal either at room temperature or when heated. Although it has been found that acetic acid is relatively more effective at biofilm removal when heated than at room temperature, long-term exposure to disinfectants such as acetic acid can deleteriously affect the piping material. Peracetic acid is effective at biofilm removal at both room temperature and when heated, but long-term exposure to acidic disinfectants such as peracetic acid can deleteriously affect dialysis machine hydraulics, including piping and chamber material.

Yet another problem with biofilm build-up in dialysate lines and dialysis pathway components is the infiltration of biofilm during valve opening for heat disinfection. Biofilm components and bacteria can dislodge or break-off and be carried into the inflow side of a component, piping or tubing. Biofilm affects not only the lifetime of hydraulic components in the dialysate side of a hemodialysis machine but also the quality of dialysate used.

SUMMARY OF THE PRESENT INVENTION

A feature of the present invention is to optimize cleaning and disinfection procedures used for hemodialysis systems.

A further feature of the present invention is to provide a method to detach and neutralize biofilm from hemodialysis machine hydraulics.

A further feature of the present invention is to reduce the buildup of biofilm in a drain line by using ultrasonic transducers to create bubbles in spent dialysate.

A further feature of the present invention is to utilize ultrasonics and ionization to breakup and prevent formation of biofilm in a dialysate pathway, particularly at points along the pathway which are prone to biofilm build-up.

A further feature of the present invention is to provide a long-lasting hydraulic system for a hemodialysis machine, and a cost savings in terms of components and labor for maintenance.

A further feature of the present invention is to provide a hydraulic system for a hemodialysis machine, of increased reliability.

According to various embodiments of the present invention, by targeting locations in dialysis machine hydraulics where biofilm is most likely to accumulate, ultrasonic heads can be used to keep fluid at those locations flowing smoothly and to inhibit bacterial growth and biofilm build-up. Alternatively, or additionally, ionizing a dialysate effluent can be used as a method of reducing, detaching, neutralizing, and removing biofilm from hemodialysis machine hydraulics. Dual-action copper anodes and aluminum/iron anodes, for example, can be used to anti-foul the hydraulics.

According to various embodiments, a combination of ionization and ultrasonication is used for reducing, detaching, neutralizing, and removing biofilm. Gaseous cavitation from ultrasonication can be caused and used to create shockwaves of ionizing particles that attack bacteria in the dialysis machine hydraulics.

According to various embodiments of the present invention, a combination of ionization and ultrasonication is implemented during a pause in the flow of a dialysate pathway cleaning liquid.

Additional features and advantages of the present invention will be set forth in part in the description that follows, and in part will be apparent from the description, or may be learned by practice of the present invention. The objectives and other advantages of the present invention will be realized by means of the elements and combinations particularly pointed out in the description and appended claims.

It is to be understood that both the foregoing general description and the following detailed description are exemplary and explanatory only and are intended to provide a further explanation of the present invention, as claimed.

The accompanying drawings, which are incorporated in and constitute a part of this application, illustrates various features of the present invention and, together with the description, serve to explain the principles of the present invention.

DETAILED DESCRIPTION OF THE PRESENT INVENTION

Figure 1A:
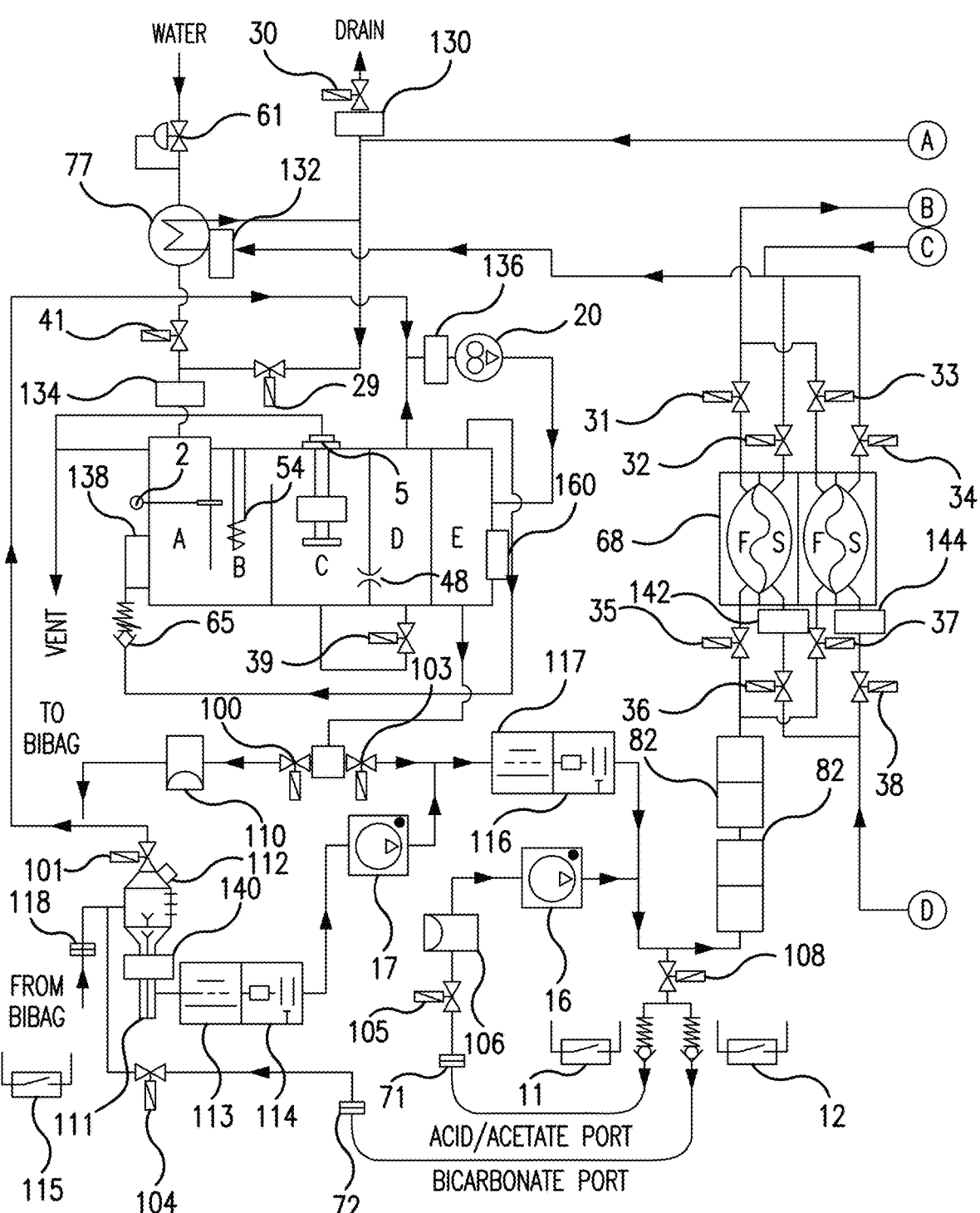
FIGS. 1A and 1B are parts one and two of a schematic diagram illustrating exemplary locations for the positions of ultrasonic generators and ultrasonic sensors in a dialysate pathway, in accordance with various embodiments of the present invention.

According to various embodiments of the present invention, ultrasonication is used to generate ultrasonic waves along a dialysate pathway. As the ultrasonic waves move through liquid in a dialysate pathway, the waves shove or move the liquid molecules, creating volumes of high pressure and volumes of low pressure. It is easier for the liquid, especially aqueous liquids, to vaporize at lower pressures, and, as such, bubbles can be made to form in the volumes of low pressure. The bubbles are lighter than the surrounding liquid so the bubbles begin to move around, for example, to rise in the liquid. As the bubbles move from the volumes of low pressure they encounter volumes of high pressure and collapse in a process of gaseous cavitation. The collapse of the bubbles releases shock waves, specifically, ultrasonic waves, that break-up and dislodge biofilm that has built-up in the dialysate pathway.

According to various embodiments of the present invention, and as another method of reducing, detaching, neutralizing, and removing biofilm from hemodialysis machine hydraulics, ionization is used to provide antifouling ions in a dialysate pathway. The antifouling ions can be produced in sufficient concentration to provide ionizing particles that attack bacteria in the pathway. One or more ionization pathways can be formed by using at least one pair of ionization electrodes. Ionization can be used instead of, or in addition to, ultrasonication, to provide antifouling ions.

According to various embodiments of the present invention, a hydraulic system is provided for an extracorporeal blood treatment device. The hydraulic system includes a dialysate pathway, at least one pump, an ultrasonic device or generator, and a controller or control system. The dialysate pathway comprises a dialyzer discharge line configured to connect to an outlet of a dialyzer, and a drain line. The at least one pump is operationally configured to move a cleaning liquid through the dialysate pathway. The at least one pump can be configured to move the cleaning liquid from the dialyzer discharge line to the drain line, and can comprise, for example, a dialysate pump. The at least one ultrasonic device can be configured to generate ultrasonic waves and can be positioned along the dialysate pathway so as to propagate the ultrasonic waves along at least a portion of the dialysate pathway. The controller can be electrically connected to the at least one pump and to the at least one ultrasonic device.

According to various embodiments, the controller can be configured to activate the at least one pump to direct a flow of cleaning liquid in the dialysate pathway from the dialyzer discharge line to the drain line. The flow can be directed during a cleaning mode. The controller can further be configured to activate the at least one ultrasonic device during the cleaning mode. The controller can further be configured to pause activation of the at least one pump while activating the at least one ultrasonic device, during the cleaning mode.

According to various embodiments, the dialyzer discharge line can comprise a connector end configured to be connected to the outlet of a dialyzer. The hydraulic system can further comprise an ionizing anode pair electrically connected to the controller. The ionizing anode pair can include at least one ionizing anode situated in the dialyzer discharge line between the connector end and the drain line. The ionizing anode pair can also comprise a second anode situated in the drain line. The ionizing anode pair can comprise a copper anode and a complimentary anode comprising at least one of an aluminum material and a ferrous material. The copper anode and the complimentary anode can be situated within the dialyzer discharge line and the controller can be configured to supply current to the copper anode and to the complimentary anode during the cleaning mode. In an exemplary embodiment, the dialyzer discharge line comprises a tubing and the anode is a copper anode, for example, in the form of a copper ring. The complimentary anode can be a second anode ring, and the copper ring and the second anode ring can be disposed within, and surrounded by, the tubing.

The hydraulic system can further comprise a cleaning liquid within the dialysate pathway. The at least one ultrasonic device can be configured to generate ultrasonic waves in the dialysate pathway, to create low pressure volumes of the cleaning liquid in the dialysate pathway, and to create high pressure volumes of the cleaning liquid in the dialysate pathway. The low-pressure volumes can be of such a low pressure as to generate gaseous bubbles. The high-pressure volumes can be of such high pressure as to rupture the gaseous bubbles. The generation and rupturing of the gaseous bubbles can break-up and dislodge biofilm built-up within the hydraulic system.

The at least one ultrasonic device can be at least one of a piezoelectric transducer, a magnetostriction transducer, an electrostriction transducer, an optoacoustic transducer, an acoustic cavitation transducer, a mechanical vibration transducer, a combination thereof, or the like. The at least one ultrasonic device can be configured to propagate ultrasonic waves at a sweep frequency. A plurality of ultrasonic devices can be provided in the hydraulic system, for example, at least two ultrasonic devices, at least three ultrasonic devices, at least four ultrasonic devices, or more.

The dialyzer discharge line can comprise a tubing and the at least one ultrasonic device can comprise a collar that surrounds the tubing. The at least one ultrasonic device can be configured to propagate ultrasonic waves radially inwardly toward a center of the tubing. The collar can comprise a piezoelectric material. In some embodiments, the dialyzer discharge line can comprise a tubing having a central axis, and the at least one ultrasonic device can be configured to propagate ultrasonic waves axially along the tubing. The at least one ultrasonic device can comprise or further comprise an ultrasonic device coupled to the drain line.

According to various embodiments, the dialysate pathway can comprise a dialyzer feed line configured to connect to an inlet of a dialyzer, and a bypass system. The controller can be electrically connected to the at least one bypass system. The bypass system can comprise a bypass line fluidly connecting the dialyzer feed line with the dialyzer discharge line. The bypass system can comprise one or more valves configured to be actuated by the controller, during a cleaning mode, to direct a flow of liquid in the dialysate pathway from the dialyzer feed line to the dialyzer discharge line, for example, without the flow passing through a dialyzer. The controller can be configured to operate in preparation for a cleaning mode, by actuating the one or more valves such that liquid in the dialysate pathway is conveyed from the dialyzer feed line, through the bypass line, and into the dialyzer discharge line.

According to various embodiments, the dialyzer feed line, the dialyzer discharge line, the bypass line, or a combination thereof, can comprise a tubing. The at least one ultrasonic device can comprise a collar that surrounds the tubing, and the at least one ultrasonic device can be positioned or otherwise configured to propagate ultrasonic waves radially inwardly toward the center of the tubing. The at least one ultrasonic device can comprise a first ultrasonic device coupled to the dialysate feed line and a second ultrasonic device coupled to the dialysate discharge line. The at least one ultrasonic device can comprise an ultrasonic device coupled to the bypass line. The at least one ultrasonic device can comprise a first ultrasonic device coupled to the dialysate feed line, a second ultrasonic device coupled to the dialysate discharge line, and a third ultrasonic device coupled to the bypass line.

According to various embodiments, the dialysate pathway can further comprise a balancing device. The balancing device can comprise a balancing chamber, a balancing feed line that leads to the balancing chamber and is configured to supply dialysate from a dialysate source into the balancing chamber, and a balancing discharge line that leads away from the balancing chamber and is configured to carry spent dialysate away from the balancing chamber. The balancing discharge can lead away from the balancing chamber and carry spent dialysate into the drain line. The dialyzer feed line can extend from the balancing chamber and can be configured to supply dialysate from the balancing chamber to a dialyzer during hemodialysis. The dialyzer discharge line can extend to the balancing chamber and can be configured to supply spent dialysate from the dialyzer into the balancing chamber during hemodialysis. The at least one ultrasonic device can be configured to generate ultrasonic waves in the balancing chamber during the cleaning mode.

According to various embodiments, the hydraulic system can further comprise a dialyzer having a dialyzer inlet and a dialyzer outlet. The dialyzer feed line can be connected to the dialyzer inlet. The dialyzer discharge line can be connected to the dialyzer outlet. The one or more valves of the bypass system can be configured to shut-off the bypass line during a treatment mode so that liquid in the dialysate pathway flows from the dialyzer feed line, into the dialyzer, through the dialyzer, out of the dialyzer outlet, and into the dialyzer discharge line. The controller can be configured to not activate the at least one ultrasonic device during the treatment mode.

In yet other embodiments of the present invention, a method is provided for operating a hydraulic system of an extracorporeal blood treatment device. The method is especially useful in a hydraulic system comprising a dialyzer discharge line and a drain line. The method can comprise disconnecting the dialyzer discharge line from a dialyzer, and/or interrupting a communication between the dialyzer discharge line and the dialyzer. The method can involve flowing a cleaning liquid from the dialyzer discharge line to the drain line. The method can comprise generating ultrasonic waves with an ultrasonic generator disposed along the dialyzer discharge line. The method can comprise propagating the ultrasonic waves from the dialyzer discharge line toward the drain line during the cleaning mode of operation of the extracorporeal blood treatment device.

According to various embodiments, the method can comprise pausing the flow of cleaning liquid for a length of time while propagating the ultrasonic waves from the dialyzer discharge line toward the drain line. The method can comprise draining the cleaning liquid from the drain line to a drain, while propagating the ultrasonic waves from the dialyzer discharge line toward the drain line. The method can comprise pausing the flow of cleaning liquid for a length of time while propagating the ultrasonic waves from the dialyzer discharge line toward the drain line.

According to various embodiments, the method can be used with a hydraulic system that further comprises a dialyzer feed line and a bypass system. The bypass system can comprise a bypass line fluidly connecting the dialyzer feed line with the dialyzer discharge line. The bypass system can comprise one or more valves configured to direct a flow of liquid in the hydraulic system from the dialyzer feed line to the dialyzer discharge line, without passing through a dialyzer. The method can yet further comprise actuating the one or more valves of the bypass system such that liquid in the hydraulic system is conveyed from the dialyzer feed line, through the bypass line, and into the dialyzer discharge line, without passing through a dialyzer.

According to various embodiments, the method can further comprise recirculating a cleaning liquid in the hydraulic system during propagation of ultrasonic waves. The method can involve draining the cleaning liquid from the hydraulic system, through the drain line, during the propagation of ultrasonic waves. In some embodiments, the hydraulic system can further comprise a dialyzer having an inlet and an outlet. The dialyzer feed line can be connected to the dialyzer inlet. The dialyzer discharge line can be connected to the dialyzer outlet. The method can further comprise flowing a dialysate through the dialyzer during a treatment mode, before actuating the one or more valves of the bypass system. The one or more valves can then be actuated, during the cleaning mode, for example, after disconnecting of the dialyzer discharge line from the dialyzer. The method can enable liquid in the hydraulic system to be conveyed from the dialyzer feed line, through the bypass line, and into the dialyzer discharge line, without passing through a dialyzer.

During the treatment mode, the dialyzer feed line can supplied with a supply of the dialysate. During the cleaning mode, the dialyzer feed line can be supplied with a cleaning liquid. The cleaning liquid can be a bleach-free cleaning liquid, an acid-free cleaning liquid, water, sterile water, hot water, a combination thereof, or the like.

According to yet further embodiments of the present invention, the method can comprise activating an ionizing anode pair during the cleaning mode. The ionizing anode pair can comprise at least one ionizing anode situated in the dialyzer discharge line upstream of the drain line. The ionizing anode pair can comprise a second anode situated in the drain line. The ionizing anode pair can comprise, for example, a copper anode and a complimentary anode, for example, comprising at least one of an aluminum material and a ferrous material. The copper anode and the complimentary anode can be situated within the dialyzer discharge line, or elsewhere. Activating the ionizing anode pair can comprise supplying an electrical current to the copper anode and to the complimentary anode, during the cleaning mode.

According to various embodiments, the method can involve activating the ionizing anode pair while generating ultrasonic waves. The method can comprise, for example, pausing generation of ultrasonic waves, and activating the ionizing anode pair while the generation of ultrasonic waves is paused. According to various embodiments, generating ultrasonic waves can be used to create low pressure volumes of cleaning liquid within the hydraulic system. The generating of ultrasonic waves can also create high pressure volumes of cleaning liquid within the hydraulic system. The low-pressure volumes can be of such low pressure as to generate gaseous bubbles in the cleaning liquid within the hydraulic system. The high-pressure volumes can be of such high pressure as to rupture gaseous bubbles in the cleaning liquid within the hydraulic system.

The flowing of cleaning liquid in the hydraulic system can be caused or effected by a dialysate pump, for example, by the same dialysate pump that moves dialysate during a treatment mode. The method can comprise activating the dialysate pump while the ultrasonic generator is activated, during the cleaning mode. In some embodiments, flow of the cleaning liquid can be caused by the dialysate pump, and the method can comprise deactivating the dialysate pump to pause the flow of the cleaning liquid, while the ultrasonic generator is activated during the cleaning mode.

The ionization anodes can be located along a dialysate pathway post-dialyzer, to prevent metal ions from getting into a blood circuit. Ultrasonic generators or heads can be positioned throughout the fresh and spent dialysate path. Although for certain drain systems, including those with longer drain tubes, relatively more time is typically required for heat or chemical disinfections. Reducing biofilm according to the present invention, however, translates into a reduced cleaning and disinfection time, the enablement of a dialysis machine to be ready for a next patient sooner, and a savings of money. Furthermore, preventing biofilm build-up in the most vulnerable parts of hemodialysis machine hydraulics results in longer-lasting components, less heat and chemical consumption, and a reduced maintenance schedule.

The system and method for reducing biofilm build-up, according to the present invention, can be used during a cleaning mode of a dialysis machine. During such a cleaning mode, non-disposable portions of a dialysate pathway can be made to bypass a dialyzer or dialyzer connectors. Herein, the term "dialysate pathway," unless specified differently, refers to all conduits and components used to prepare and heat fresh dialysate and all conduits and components used to handle and drain spent dialysate. As such, herein, components including BIBAG components, sampling port components, acid/acetate port components, bicarbonate port components, heater components, air separation components, mixing chambers, balance chambers, hydrochambers, other chambers, spent dialysate lines, water inlet lines, filters, and all tubing, conduits, and other plumbing associated therewith the dialysate side of the dialysis machine.

Bypassing the dialyzer can be effected, for example, by using one or more bypass valves, one or more recirculation valves, a combination thereof, or the like. Through plumbing and valving, a recirculating dialysate circuit can be formed. When plumbed for a recirculating circuit, a cleaning solution, for example, hot water, can be recirculated over and over through non-disposable portions of the dialysate pathway. Alternatively, or additionally, single pass cleaning pathways can be formed to clean non-disposable portions of the dialysate pathway. During recirculating flow or during single pass flow, the ultrasonic generators, also referred to herein as sonotrodes, can be triggered or activated to generate ultrasonic waves that propagate through at least a respective adjacent portion or length of the dialysate pathway. Spacing apart a number of different ultrasonic generators, along various lengths, stretches, portions, or sections of the dialysate pathway, can ensure that strong ultrasonic waves are propagated throughout the dialysate pathway and thus efficiently break-up and dislodge biofilm throughout the entire dialysate pathway. According to various embodiments, the ultrasonic generators can be triggered or activated to generate ultrasonic waves during a pause in recirculating flow or during a pause in single pass flow.

The ultrasonic generators, sonicators, or sonotrodes that can be used in the present invention are commercially available, such as from Beijing Ultrasonic. Particular examples include the 300W Immersible Ultrasonic Transducer and similar models.

In general, with respect to the sonication, any one or more of the sonications can be conducted at an oscillation frequency of at least 20 kHz, such as from 20 kHz to 50 MHz.

One or more of the individual sonicators can have a power rating of at least 25 watts, or at least 50 watts, or at least 100 watts, or at least 150 watts, or at least 200 watts, such as from 25 watts to 1500 watts, or from 100 watts to 1500 watts, or from 200 watts to 1000 watts or from 400 watts to 800 watts and the like.

The sonication used can be a swept-frequency mode of sonication. This mode is where the frequency is changed at a certain rate (e.g., one frequency for a period of time, and then a second frequency for a period of time, and then a third frequency for a period of time). Each sonicator can be tuned to emit a specific one of a variety of different frequencies.

The sonication can be conducted with an ultrasonic apparatus. Examples include a tip sonicator or probe sonicator. Other examples include a bath sonicator.

As an option, the sonication can be a pulsed mode of sonication. As an option, the sonication can be a continuous mode of sonication (i.e., continuous sonication).

When the sonication occurs the dialysate pathway can be moving, paused, or stagnant.

The sonication, depending on where the sonication occurs and/or how the sonicator is used or located, can be direct sonication or can be indirect sonication.

The sonication can be conducted with an ultrasonic homogenizer or probe sonicator.

The dialysate pathway portion to be sonicated can have a volume of liquid, and the sonication can, as an option, occur at a power rating of sonication per gallon of liquid in the bath so as to achieve a rating of at least 0.1 watt/gallon or at least 0.2 watt/gallon (e.g., at least 0.3 watt/gallon, at least 0.4 watt/gallon, at least 0.5 watt/gallon, at least 0.6 watt/gallon, or at least 0.8 watt/gallon, such as from 0.1 watt/gallon to 1 watt/gallon or from 0.2 watt/gallon to 1 watt/gallon).

Figure 1B:
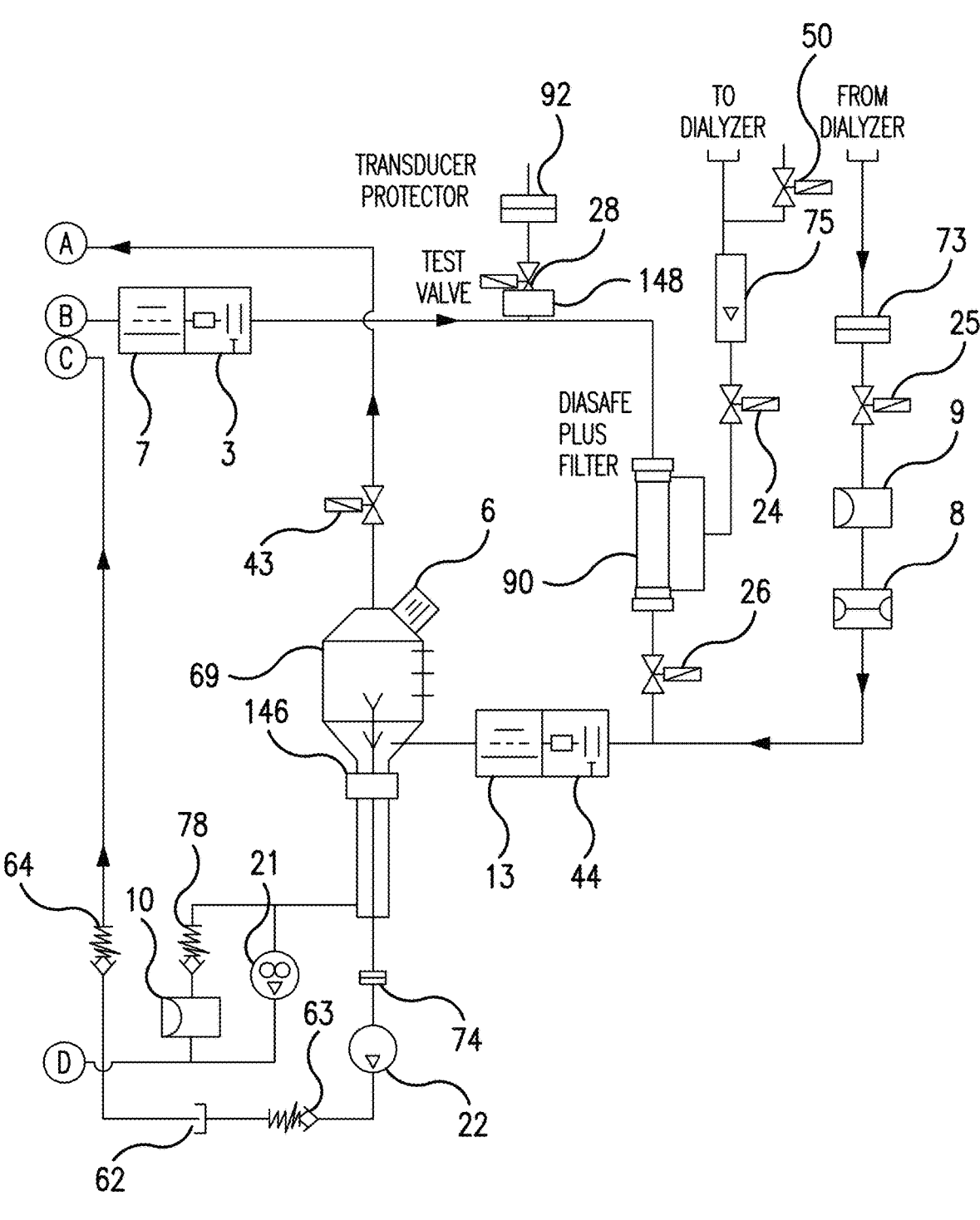

With reference now to the drawing figures, FIGS. 1A and 1B are two portions of an exemplary dialysate circuit or pathway, that together make up most of the entirety of an exemplary dialysate circuit or pathway with which the present invention can be implemented. Line terminations depicted as the circled A, B, C, and D in FIG. 1A connect with line terminations depicted as the circled A, B, C, and D, respectively, in FIG. 1B. As can be seen in FIGS. 1A and 1B, the dialysate circuit or pathway to and from the dialyzer includes many components. A temperature control thermistor 2 is provided as are a temperature monitor thermistor 3, a float switch 5, a conductivity cell 7, a blood leak detector 8, a dialysate pressure transducer 9, and a chamber full switch 10. An air sensor 6 is provided in an air separator chamber 69. A reed switch concentrate connector 11 is provided as is a reed switch bicarbonate connector 12. A post conductivity cell 13 is located adjacent to a post temperature thermistor 44. A number of pumps are provided, including a concentrate pump 16, a bicarbonate pump 17, a deaeration pump 20, a flow pump 21, and an ultrafiltration pump 22.

The dialysate pathway is also provided with many valves, including a first dialyzer valve 24, a second dialyzer valve 25, a bypass valve 26, a test valve 28, a recirculation valve 29, a drain valve 30, a first balance chamber valve 31, a second balance chamber valve 31, a third balance chamber valve 33, a fourth balance chamber valve 34, a fifth balance chamber valve 35, a sixth balance chamber valve 36, a seventh balance chamber valve 37, and an eighth balance chamber valve 38. Other valves along the dialysate pathway include a bypass valve 39 for a deaeration orifice 48, a water inlet valve 41, a vent valve 43 for air separation chamber 69, a sampling valve 50, a check valve 63 between ultrafiltration pump 22 and a sample port 62, a check valve 64 between sample port 62 and a drain, a loading pressure valve 65, a flow pump pressure relief valve 78, a BIBAG fill valve 100, a BIBAG vent valve 101, a hydrochamber outlet valve 103, a bicarbonate port valve 104, an acid port valve 105, and a rinse port valve 108.

A hydro block or hydrochamber is provided that comprises a series of five sub-chambers including: chamber A, an inlet water chamber; chamber B, a heater chamber; chamber C, a float chamber; chamber D, a deaeration chamber; and chamber E, an air removal chamber. The reference letters designating these sub-chambers are not circled in FIGS. 1A and 4A.

A plurality of filters is also provided along the dialysate circuit or pathway, including an acid/acetate filter 71, a bicarbonate filter 72, a from-dialyzer line filter cartridge 73, an ultrafiltration pump filter 74, a DIASAFE® plus filter 90 (available from Fresenius Medical Care Deutschland GmbH of Bad Homburg, Germany), and a BIBAG filter 118. Also along the dialysate pathway are a heater 54, a water inlet pressure regulator 61, a balance chamber 68, a dialysate line flow indicator 75, a heat exchanger 77, two mixing chambers 82, a transducer protector 92, an acid port pressure transducer 106, a BIBAG pressure transducer 110, a BIBAG air separation chamber 111, a BIBAG air separation chamber air sensor 112, a BIBAG conductivity cell 113, a BIBAG temperature thermistor 114, a BIBAG present switch 115, a bicarbonate temperature thermistor 116, and a bicarbonate conductivity cell 117.

As can be seen in FIGS. 1A and 1B, a plurality of ultrasonic generators or sonotrodes is provided along the dialysate pathway, including many at different locations. The ultrasonic generators include ultrasonic generators 130, 132, 134, 136, 138, 140, 142, 144, 146, and 148. Any number of ultrasonic generators can be included according to various embodiments. For example, all of ultrasonic generators 130, 132, 134, 136, 138, 140, 142, 144, 146, and 148, shown in FIGS. 1A and 1B, can be included. One or more ultrasonic sensors can be provided along the dialysate pathway, for example, including, but not limited to, ultrasonic sensor 160. The or other ultrasonic sensors can be provided along the dialysate pathway and can be configured to sense the frequency of ultrasonic waves generated by the ultrasonic generators and propagated along the dialysate pathway.

As is shown in FIGS. 1A and 1B, ultrasonic sensor 160 is located in an intermediate position along the dialysate pathway. One or more other ultrasonic sensors can be provided along the dialysate pathway, and, like ultrasonic sensor 160, can be configured to sense the frequency of ultrasonic waves generated by the ultrasonic generators, which are propagated along the dialysate pathway. Frequencies sensed by the ultrasonic sensor can be measured. Corresponding measurement signals can be generated by the ultrasonic sensor and sent to a processor 200, as shown in FIG. 2.

Figure 2:
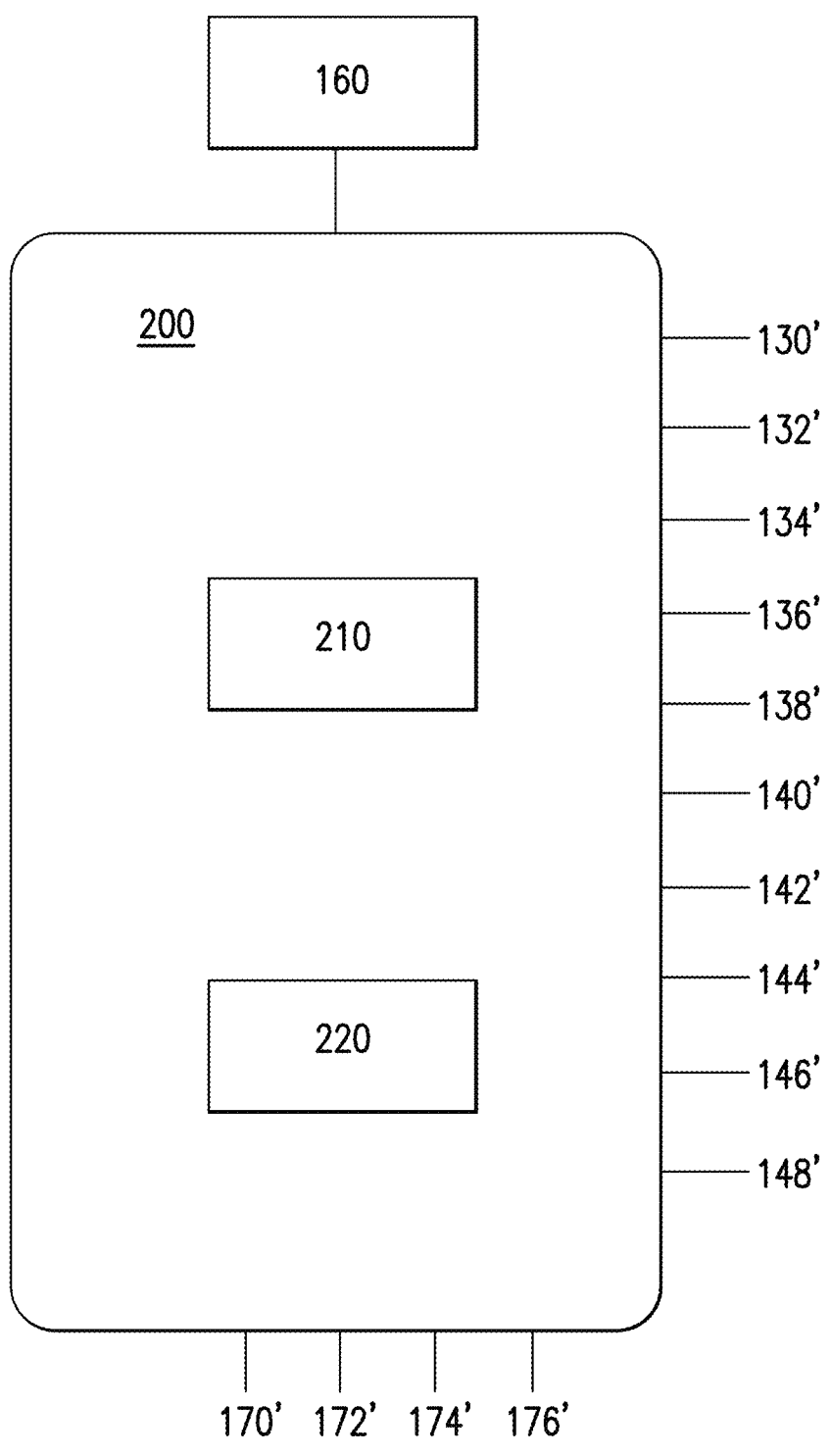
FIG. 2 is a schematic diagram of a processing system that includes a processor, a computing unit, and a memory, and electrical leads connecting the processing system to the ultrasonic generators, ultrasonic sensor, and ionization anodes shown in FIGS. 1A, 1B, 4A, and 4B.

As seen in FIG. 2, processor 200 includes a computing unit 210 and a memory 220. Processor 200 receives signals from ultrasonic sensor 160 (FIGS. 1A and 1B) sent through a signal line 160' that provides an electrical communication between ultrasonic sensor 160 and processor 200. Processor 200 receives signals from ultrasonic sensor 160, and the signals correspond to ultrasonic frequencies measured by ultrasonic sensor 160. In an exemplary processor, computing unit 210 compares the measured frequencies to frequencies stored in memory 220 and determines whether an adjustment needs to be made to the frequencies being generated by one or more of ultrasonic generators 130, 132, 134, 136, 138, 140, 142, 144, 146, and 148 (FIGS. 1A and 1B). For fine tuning, processor 200 can send triggering signals independently to each ultrasonic generator, one at a time, so that the frequency or frequencies generated by each respective ultrasonic generator can be measured, one at a time. The triggering signals can be sent to the ultrasonic generators along data lines 130', 132', 134', 136', 138', 140', 142', 144', 146', and 148' that provide electrical communications to ultrasonic generators 130, 132, 134, 136, 138, 140, 142, 144, 146, and 148, respectively. By independently measuring the frequencies, each ultrasonic generator can be tuned to the same ultrasonic frequency.

In some embodiments, all of the ultrasonic generators can be tuned to same frequency. In some embodiments, one or more of the ultrasonic generators can be tuned to a different frequency compared with one or of the other ultrasonic generators. The frequencies of the ultrasonic generators can be tuned to maximize the production of destructive, biofilm-disrupting ultrasonic waves.

Figure 4A:
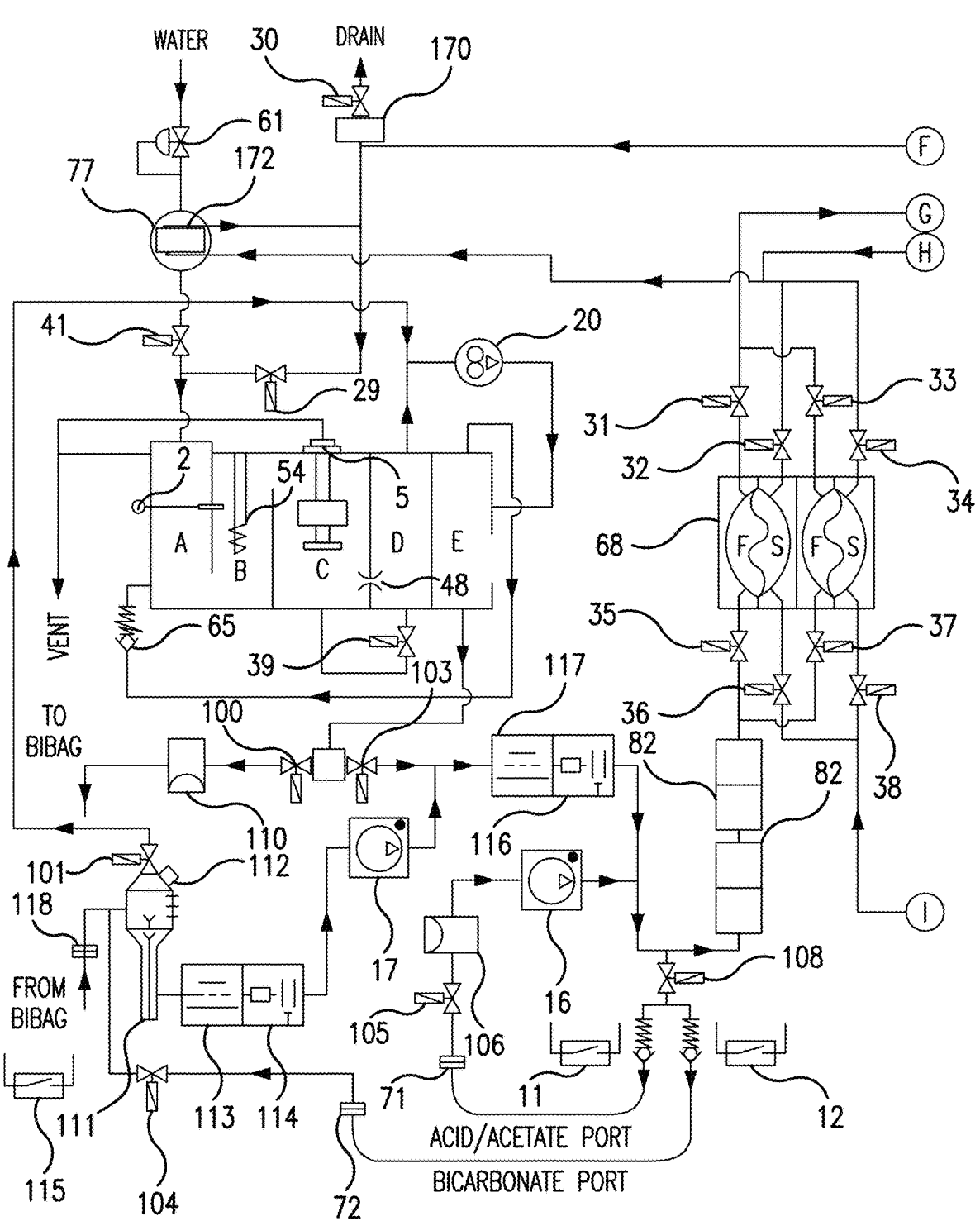
FIGS. 4A and 4B are parts one and two of a schematic diagram illustrating exemplary locations for the positions of ionization anodes in a dialysate pathway, in accordance with various embodiments of the present invention.
Figure 4B:
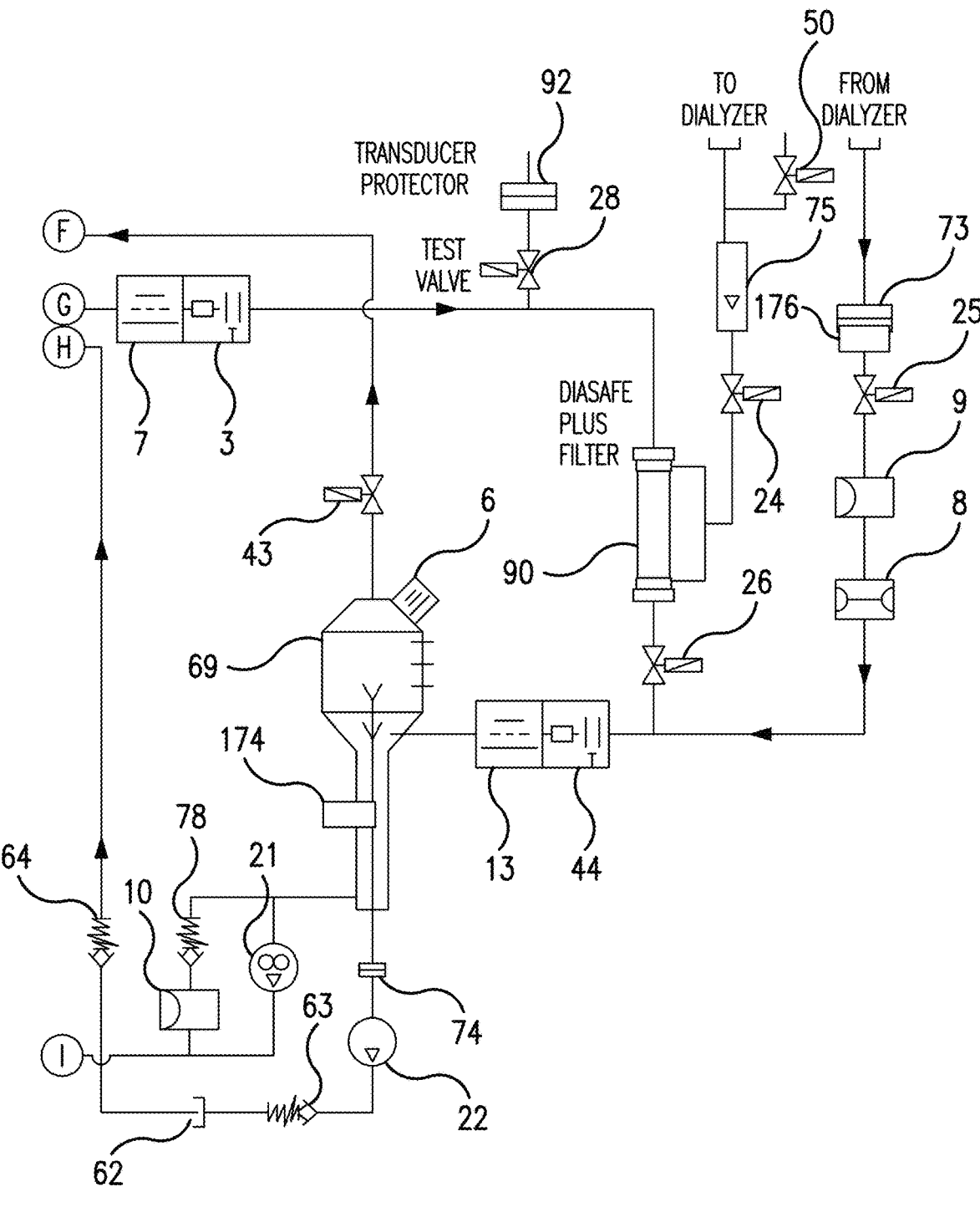

Also shown in FIG. 2 are data lines 170', 172', 174', and 176' in electrical communication with a plurality of anti-fouling anodes, for example, antifouling electrodes 170, 172, 174, and 176 as shown in FIGS. 4A and 4B. Processor 200 can send triggering signals independently to each of antifouling electrodes 170, 172, 174, and 176, for example, one at a time. The triggering signals can be sent to the antifouling electrodes, along data lines 170', 172', 174', and 176', respectively. By independently sending triggering signals, the antifouling electrodes 170, 172, 174, and 176 can be triggered in different pairs to form different ionization pathways for the movement of antifouling ions from one location of the dialysate pathway to another location. Each pair of triggered antifouling electrodes can include a first electrode of a first metal, and a second electrode of a second metal that more readily loses electrons than the first metal. For example, a triggered pair can include a zinc electrode and a copper electrode, or the pair can include a silver electrode and a copper electrode, or the pair can include an iron electrode and a copper electrode. Other metal electrode pairs can be used. Both electrodes of the pair are in electrical communication with each other through a dialysate pathway cleaning liquid or solution, for example, that contains elec-trolytes. As such, the electrodes and the pathway electrically connecting them constitute an electrochemical cell, akin to a voltaic, galvanic cell. Any two conducting materials or metals that have reactions with different standard potentials can form the electrochemical cell.

Figure 3A:
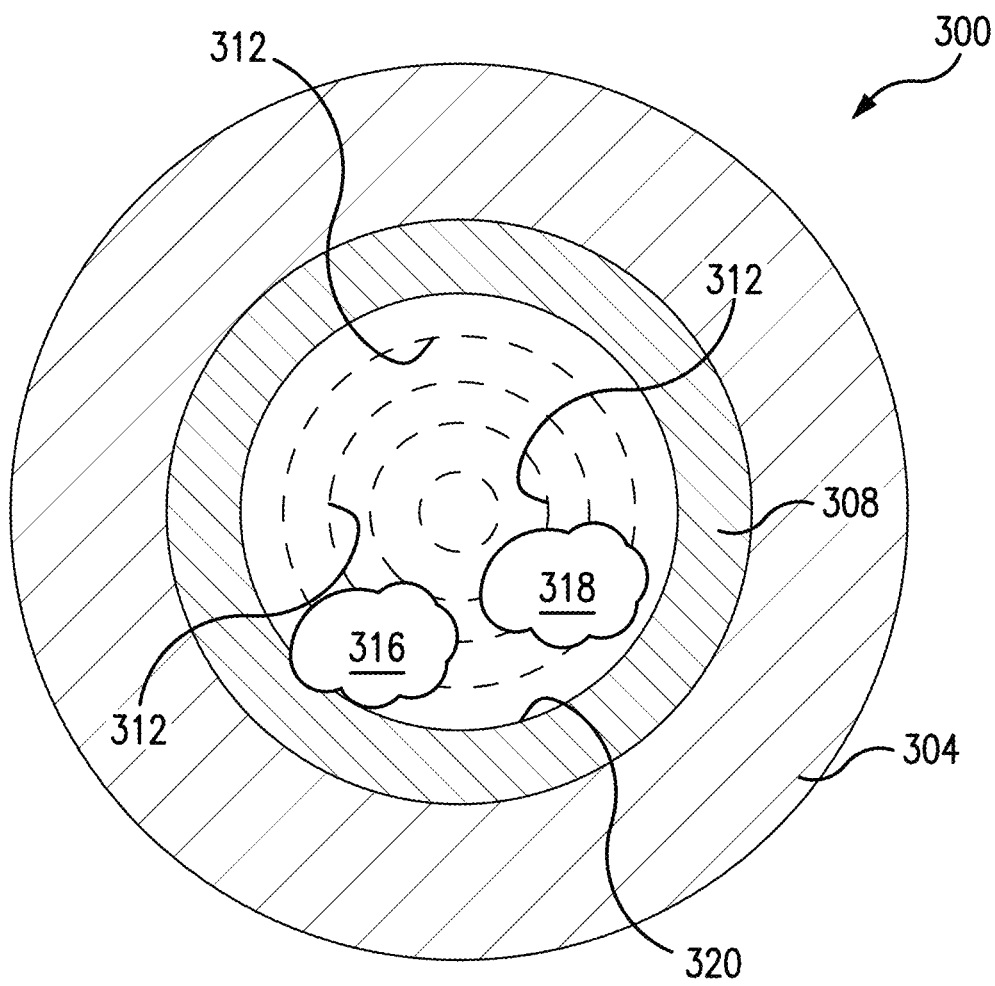
FIG. 3A is a cross-sectional view of an ultrasonic cleaning system according to various embodiments of the present invention, which includes a piezoelectric collar fitted around a length of tubing that is part of a dialysate pathway in a dialysis machine, and also depicts ultrasonic waves and biofilm build-up that has been dislodged from the inner surface of the tubing.
Figure 3B:
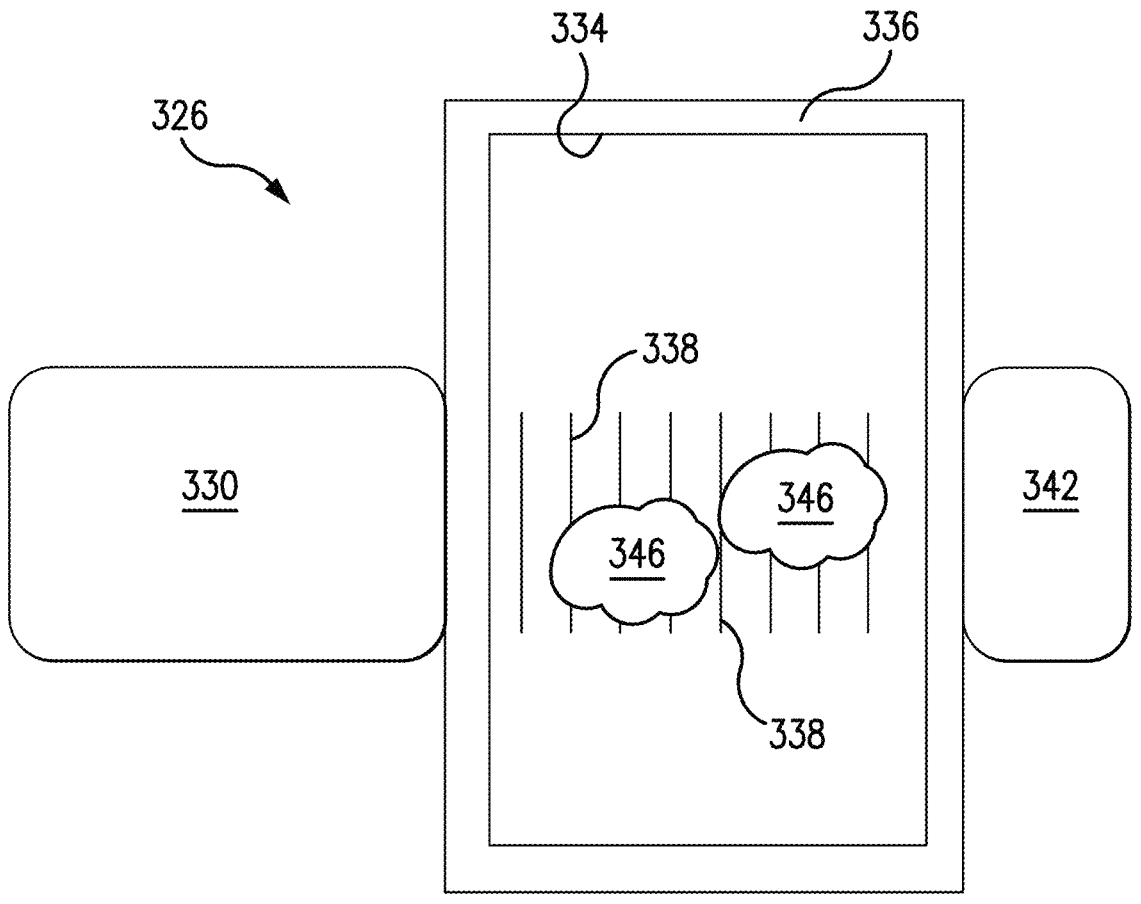
FIG. 3B is a schematic diagram of another ultrasonic cleaning system according to various embodiments of the present invention, which includes a piezoelectric head adjacent to and in contact with a chamber that is part of a dialysate pathway, and also depicts ultrasonic waves propagating through the chamber and dislodging and/or shredding biofilm that had formed on inside surfaces of the chamber.

FIGS. 3A and 3B schematically illustrate two different ultrasonic cleaning systems according to various embodi-ments of the present invention. In FIG. 3A, an ultrasonic cleaning system 300 is shown in cross-section and includes a piezoelectric collar 304 fitted around a length of tubing 308 that is part of a dialysate pathway in a dialysis machine. Length of tubing 308 can be situated in a dialysate pathway, for example, between either a disposable dialyzer outlet or a dialysate bypass valve, and a dialysate drain. In other embodiments, length of tubing 308 can be situated in a dialysate pathway between, for example, a dialysate prepa-ration component and either an inlet to a disposable dialyzer or a dialyzer bypass valve.

Biofilm that has built-up or is building-up inside length of tubing 308, can be dislodged or shredded by ultrasonic waves 312 generated by piezoelectric collar 304. Triggering signals can be sent along one or more data lines, from a processor such as processor 200 shown in FIG. 2, to piezo-electric collar 304. The data signals can actuate piezoelectric collar 304 and cause ultrasonic waves 312 to be generated within length of tubing 308. As an example, ultrasonic waves 312 can be powerful enough to dislodge a biofilm mass 316 that is stuck to an inner surface 320 of length of tubing 308, to form a dislodged biofilm mass, such as dislodged biofilm mass 318. A dialysate pathway cleaning solution can be flowed through a dialysate pathway includ-ing length of tubing 308 to carry away the dislodged biofilm. The dislodged biofilm can be carried away, for example, to a drain and out of the dialysate pathway.

In another embodiment of an ultrasonic cleaning system according to the present invention, and as shown in FIG. 3B, an ultrasonic cleaning system 326 is provided that includes a piezoelectric head 330 adjacent to and in contact with a chamber 334 inside a dialysis machine, for example, along a dialysate pathway. Chamber 334 is defined by a chamber sidewall 336. Piezoelectric head 330 generates ultrasonic waves 338 that propagate through chamber 334 and dislodge and/or shred biofilm 346 that has formed on surfaces within chamber 334. An ultrasonic sensor 342 is positioned adja-cent and in contact with chamber 334, for example, opposite piezoelectric head 330 and in a position so as to be config-ured to measure the frequencies of ultrasonic waves 338. Frequencies measured by ultrasonic sensor 342 can be sent as data signals, along data lines, to a processor, such as processor 200 shown in FIG. 2. The processor can then compare the measured frequencies to target frequencies, and, based on the comparison, can adjust triggering signals sent to piezoelectric head 330. As such, piezoelectric head 330 can be tuned to generate ultrasonic waves of a desired frequency or within a desired frequency range.

FIGS. 4A and 4B show the same dialysate circuit or pathway shown in FIGS. 1A and 1B, and the reference numerals shown in FIGS. 4A and 4B refer to the same components shown by the same reference numerals in FIGS. 1A and 1B. For the sake of simplification, however, the ultrasonic generators and ultrasonic sensor show in FIGS. 1A and 1B are excluded from FIGS. 4A and 4B, but only so that the locations of ionization electrodes can be emphasized in FIGS. 4A and 4B. Line terminations depicted as the circled F, G, H, and I in FIG. 4A connect with line termi-nations depicted as the circled F, G, H, and I, respectively, in FIG. 4B.

In FIGS. 4A and 4B, a plurality of antifouling anodes 170, 172, 174, and 176 are shown. While the locations shown in FIGS. 4A and 4B, for the antifouling anodes, are exemplary, it is to be understood that one or more antifouling anodes can be provided in one or more different locations. One or more of the antifouling anodes can be located at or near the same location where one or more ultrasonic wave generators are located or positioned. For example, as can be seen, antifoul-ing anode 170 can be located at or near the same location where ultrasonic generator 130 is located. Antifouling anode 174 can be located at or near the same location where ultrasonic generator 146 is located.

One or more of the antifouling anodes can be battery powered. As shown, ionization anode 176 can be located within, or adjacent to, from-dialyzer line filter cartridge 73, and can be battery powered. In an example, ionization anode 176 is the only ionization anode that is battery powered. In other examples, more than one ionization anode is battery powered.

At least a pair of antifouling anodes can be provided, for example, a pair including a copper anode and an aluminum and/or iron anode. As is known, the transport of copper ions from a copper anode can be assisted by aluminum hydroxide created by an aluminum anode, which flocculates with copper released from the copper anode. The ionic products formed by the copper anodes are hostile to biofilms and other fouling and can be carried by the flow of dialysate to settle on or act on surfaces where fouling is most likely to adhere and biofilm is most likely to form. Hence, the principles of marine antifouling can be implemented in the dialysate circuit or pathway.

Figure 5:
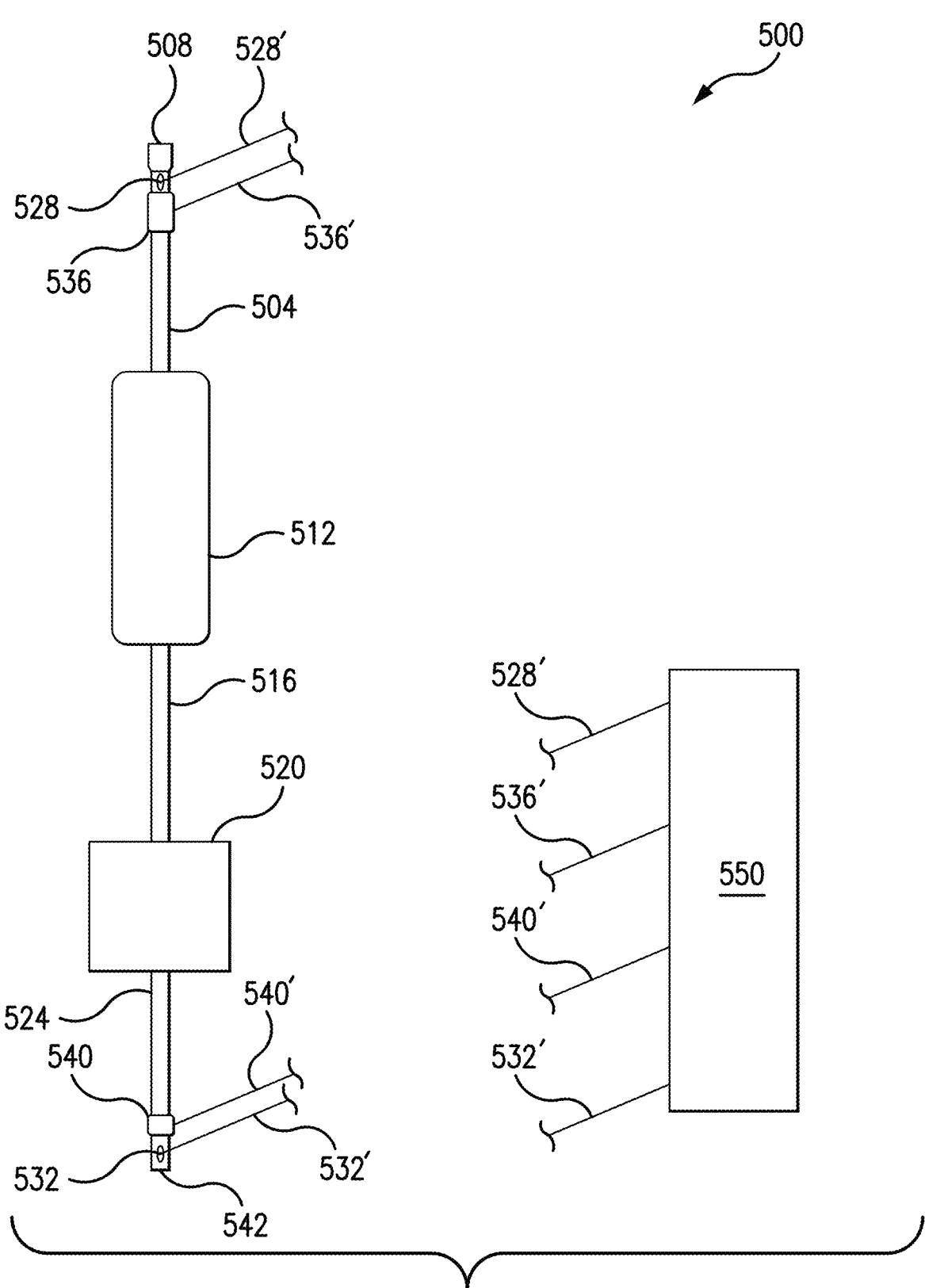
FIG. 5 is a schematic diagram illustrating exemplary locations for the positions of an ultrasonic generator, an ultrasonic sensor, and ionization anodes, in a dialysate pathway, in accordance with yet other various embodiments of the present invention.

FIG. 5 is a schematic diagram of a simplified dialysate pathway 500 according to yet another embodiment of the present invention. In FIG. 5, dialysate pathway 500 begins, in the schematic shown, with a dialyzer discharge intake coupling 508 and further includes a dialyzer discharge line 504, a spent dialysate balance chamber 512, a heat exchanger 520, a conduit 516 connecting spent dialysate balance chamber 512 with heat exchanger 520, a drain line 524, and a discharge outlet 542. Adjacent to dialyzer discharge intake coupling, and at the input end of dialyzer discharge line 504, is arranged a first ionization anode 528 and an ultrasonic generating collar 536. First ionization anode 528 is paired with a second ionization anode 532 that is located at the distal end or discharge end of dialysate pathway 500, relative to the input end of dialyzer discharge line 504.

Along, but toward the discharge end of, drain line 524, an ultrasonic sensor 540 is arranged that is configured to measure the wavelengths of ultrasonic waves that are generated by ultrasonic generating collar 536 and propagated through dialysate pathway 500. Electrical leads 536' and 540' are electrically connected at respective first ends thereof to ultrasonic generating collar 536 and ultrasonic sensor 540, respectively. Second ends of electrical leads 536' and 540' are respectively electrically connected to a processor 550. Processor 550 generates and sends activation signals along electrical lead 536' to ultrasonic generating collar 536, to activate ultrasonic generating collar 536 to produce ultrasonic waves. Processor 550 receives measurement signals sent from ultrasonic sensor 540, along electrical lead 540'. Processor 550 is equipped with a comparator or sub-processor that is configured to compare wavelength measurement signals sent from ultrasonic sensor 540 along electrical lead 540', with desired and/or predetermined wavelength measurements. Processor 550 comprises a controller that, based on the comparison, can control the processor to increase or decrease the frequencies of wavelengths generated by ultrasonic generating collar 536. By continuously, intermittently, periodically, or single occurrence comparing, the wavelengths of the ultrasonic waves generated by the collar can be fine-tuned to specifically match a desired frequency that effectively removes, destroys, dislodges, or otherwise cleans biofilm build-up from dialysate pathway 500.

In addition to, or as an alternative to, the ultrasonic cleaning described above with reference to FIG. 5, ionization anodes and an ionization pathway can be utilized to clean the dialysate pathway. As shown in FIG. 5, electrical leads 528' and 532' are electrically connected at respective first ends thereof to first ionization anode 528 and second ionization anode 532, respectively. Second ends of electrical leads 528' and 532' are respectively electrically connected to processor 550. Processor 550 generates and sends electrical signals along electrical leads 528' and 532', to first ionization anode 528 and second ionization anode 532, respectively. The electrical signals apply electrical potential to each anode and produce an ionization pathway through almost the entirety of dialysate pathway 500. First ionization anode 528 and second ionization anode 532 can thus be made to create a flow of ions along or through dialysate pathway 500 to effectively remove, destroy, dislodge, or otherwise clean biofilm build-up from dialysate pathway 500, and/or to prevent the formation and build-up of biofilm in the first place.

The system exemplified in FIG. 5 can be used during a flow of dialysate, spent dialysate, or cleaning liquid, through dialysate pathway 500, or can be used while liquid is stagnant or flow is paused in dialysate pathway 500.

The present invention includes the following aspects/embodiments/features in any order and/or in any combination:

1. The present invention relates to a hydraulic system for an extracorporeal blood treatment device comprising:

a dialysate pathway comprising a dialyzer discharge line configured to connect to an outlet of a dialyzer, and a drain line;

at least one pump operationally configured to move a cleaning liquid through the dialysate pathway from the dialyzer discharge line to the drain line;

at least one ultrasonic device configured to generate ultrasonic waves and positioned along the dialysate pathway so as to propagate the ultrasonic waves along at least a portion of the dialysate pathway; and a controller electrically connected to the at least one pump and to the at least one ultrasonic device, wherein the controller is configured to activate the at least one pump to direct a flow of cleaning liquid in the dialysate pathway from the dialyzer discharge line to the drain line, during a cleaning mode, and the controller is further configured to activate the at least one ultrasonic device during the cleaning mode.

2. The hydraulic system for an extracorporeal blood treatment device, of any preceding or following embodiment/feature/aspect, wherein, the controller is further configured to pause activation of the at least one pump while activating the at least one ultrasonic device, during the cleaning mode.

3. The hydraulic system for an extracorporeal blood treatment device, of any preceding or following embodiment/feature/aspect, wherein the dialyzer discharge line comprises a connector end configured to be connected to the outlet of a dialyzer, and the hydraulic system for an extracorporeal blood treatment device further comprises an ionizing anode pair electrically connected to the controller, the ionizing anode pair including at least one ionizing anode situated in the dialyzer discharge line between the connector end and the drain line.

4. The hydraulic system for an extracorporeal blood treatment device, of any preceding or following embodiment/feature/aspect, wherein the ionizing anode pair comprises a second anode situated in the drain line.

5. The hydraulic system for an extracorporeal blood treatment device, of any preceding or following embodiment/feature/aspect, wherein the ionizing anode pair comprises a copper anode and a complimentary anode comprising at least one of an aluminum material and a ferrous material, wherein the copper anode and the complimentary anode are situated within the dialyzer discharge line and the controller is configured to supply current to the copper anode and to the complimentary anode during the cleaning mode.

6. The hydraulic system for an extracorporeal blood treatment device, of any preceding or following embodiment/feature/aspect, wherein the dialyzer discharge line comprises a tubing, the copper anode is a copper ring, the complimentary anode is a second anode ring, and the copper ring and the second anode ring are disposed within and are surrounded by the tubing.

7. The hydraulic system for an extracorporeal blood treatment device, of any preceding or following embodiment/feature/aspect, further comprising a cleaning liquid within the dialysate pathway, wherein the at least one ultrasonic device is configured to generate ultrasonic waves in the dialysate pathway, to create low pressure volumes of the cleaning liquid in the dialysate pathway, and to create high pressure volumes of the cleaning liquid in the dialysate pathway, the low pressure volumes being of such low pressure as to generate gaseous bubbles, and the high pressure volumes being of such high pressure as to rupture the gaseous bubbles.

8. The hydraulic system for an extracorporeal blood treatment device, of any preceding or following embodiment/feature/aspect, wherein the at least one ultrasonic device is at least one of a piezoelectric transducer, a magnetostriction transducer, an electrostriction transducer, an optoacoustic transducer, an acoustic cavitation transducer, and a mechanical vibration transducer.

9. The hydraulic system for an extracorporeal blood treatment device, of any preceding or following embodiment/feature/aspect, wherein the at least one ultrasonic device is configured to propagate ultrasonic waves at a sweep frequency.

10. The hydraulic system for an extracorporeal blood treatment device, of any preceding or following embodiment/feature/aspect, wherein the dialyzer discharge line comprises a tubing, the at least one ultrasonic device comprises a collar that surrounds the tubing, and the at least one ultrasonic device propagates ultrasonic waves radially inwardly toward a center of the tubing.

11. The hydraulic system for an extracorporeal blood treatment device, of any preceding or following embodiment/feature/aspect, wherein the collar comprises a piezoelectric material.

12. The hydraulic system for an extracorporeal blood treatment device, of any preceding or following embodiment/feature/aspect, wherein the dialyzer discharge line comprises a tubing having a central axis, and the at least one ultrasonic device is configured to propagate ultrasonic waves axially along the tubing.

13. The hydraulic system for an extracorporeal blood treatment device, of any preceding or following embodiment/feature/aspect, wherein the at least one ultrasonic device further comprises an ultrasonic device coupled to the drain line.

14. The hydraulic system for an extracorporeal blood treatment device, of any preceding or following embodiment/feature/aspect, wherein:

the dialysate pathway further comprises a dialyzer feed line configured to connect to an inlet of a dialyzer, and a bypass system;

the controller is also electrically connected to the at least one bypass system;

the bypass system comprises a bypass line fluidly connecting the dialyzer feed line with the dialyzer discharge line;

the bypass system comprises one or more valves configured to be actuated by the controller, during a cleaning mode, to direct a flow of liquid in the dialysate pathway from the dialyzer feed line to the dialyzer discharge line, without passing through a dialyzer; and the controller is configured to operate in preparation for the cleaning mode, by actuating the one or more valves such that liquid in the dialysate pathway is conveyed from the dialyzer feed line, through the bypass line, and into the dialyzer discharge line.

15. The hydraulic system for an extracorporeal blood treatment device, of any preceding or following embodiment/feature/aspect, wherein the dialyzer feed line, the dialyzer discharge line, the bypass line, or a combination thereof, comprises a tubing, the at least one ultrasonic device comprises a collar that surrounds the tubing, and the at least one ultrasonic device propagates ultrasonic waves radially inwardly toward a center of the tubing.

16. The hydraulic system for an extracorporeal blood treatment device, of any preceding or following embodiment/feature/aspect, wherein the at least one ultrasonic device comprises a first ultrasonic device coupled to the dialysate feed line and a second ultrasonic device coupled to the dialysate discharge line.

17. The hydraulic system for an extracorporeal blood treatment device, of any preceding or following embodiment/feature/aspect, wherein the at least one ultrasonic device further comprises a third ultrasonic device coupled to the bypass line.

18. The hydraulic system for an extracorporeal blood treatment device, of any preceding or following embodiment/feature/aspect, wherein:

the dialysate pathway further comprises a balancing device comprising a balancing chamber, a balancing feed line that leads to the balancing chamber and is configured to supply dialysate from a dialysate source into the balancing chamber, and a balancing discharge line that leads away from the balancing chamber and is configured to carry spent dialysate away from the balancing chamber and into the drain line;

the dialyzer feed line extends from the balancing chamber and is configured to supply dialysate from the balancing chamber to a dialyzer during hemodialysis;

the dialyzer discharge line extends to the balancing chamber and is configured to supply spent dialysate from the dialyzer into the balancing chamber during hemodialysis; and the at least one ultrasonic device is configured to generate ultrasonic waves in the balancing chamber during the cleaning mode.

19. The hydraulic system for an extracorporeal blood treatment device, of any preceding or following embodiment/feature/aspect, further comprising a dialyzer having a dialyzer inlet and a dialyzer outlet, wherein the dialyzer feed line is connected to the dialyzer inlet, the dialyzer discharge line is connected to the dialyzer outlet, the one or more valves are configured to shut-off the bypass line during a treatment mode so that liquid in the dialysate pathway flows from the dialyzer feed line, into the dialyzer, through the dialyzer, out of the dialyzer outlet, and into the dialyzer discharge line, and the controller is configured to not activate the at least one ultrasonic device during the treatment mode.

20. A method of operating a hydraulic system for an extracorporeal blood treatment device, the hydraulic system comprising a dialyzer discharge line and a drain line, the method comprising:

disconnecting the dialyzer discharge line from a dialyzer;

flowing a cleaning liquid from the dialyzer discharge line to the drain line;

generating ultrasonic waves with an ultrasonic generator disposed along the dialyzer discharge line; and propagating the ultrasonic waves from the dialyzer discharge line toward the drain line during a cleaning mode of operation of the extracorporeal blood treatment device.

21. The method of any preceding or following embodiment/feature/aspect, further comprising pausing the flow of cleaning liquid for a length of time while propagating the ultrasonic waves from the dialyzer discharge line toward the drain line.

22. The method of any preceding or following embodiment/feature/aspect, further comprising draining the cleaning liquid from the drain line to a drain while propagating the ultrasonic waves from the dialyzer discharge line toward the drain line.

23. The method of any preceding or following embodiment/feature/aspect, further comprising pausing the flow of cleaning liquid for a length of time while propagating the ultrasonic waves from the dialyzer discharge line toward the drain line.

24. The method of any preceding or following embodiment/feature/aspect, wherein the hydraulic system further comprises a dialyzer feed line and a bypass system, the bypass system comprises a bypass line fluidly connecting the dialyzer feed line with the dialyzer discharge line, the bypass system comprises one or more valves configured to direct a flow of liquid in the hydraulic system from the dialyzer feed line to the dialyzer discharge line, without passing through a dialyzer, and the method further comprises actuating the one or more valves such that liquid in the hydraulic system is conveyed from the dialyzer feed line, through the bypass line, and into the dialyzer discharge line without passing through a dialyzer.

25. The method of any preceding or following embodiment/feature/aspect, further comprising recirculating the cleaning liquid in the hydraulic system during the propagating of the ultrasonic waves.

26. The method of any preceding or following embodiment/feature/aspect, further comprising draining the cleaning liquid from the hydraulic system, through the drain line, during the propagating of the ultrasonic waves.

27. The method of any preceding or following embodiment/feature/aspect, wherein the hydraulic system further comprises a dialyzer having an inlet and an outlet, the dialyzer feed line is connected to the dialyzer inlet, the dialyzer discharge line is connected to the dialyzer outlet, and the method further comprises:

flowing a dialysate through the dialyzer during a treatment mode, before the actuating of the one or more valves; and then performing the actuating of the one or more valves, during the cleaning mode, after the disconnecting of the dialyzer discharge line from the dialyzer, such that liquid in the hydraulic system is conveyed from the dialyzer feed line, through the bypass line, and into the dialyzer discharge line without passing through the dialyzer.

28. The method of any preceding or following embodiment/feature/aspect, wherein during the treatment mode, the dialyzer feed line is supplied with a supply of the dialysate, and during the cleaning mode, the dialyzer feed line is supplied with a cleaning liquid.

29. The method of any preceding or following embodiment/feature/aspect, wherein the cleaning liquid is a bleach-free cleaning liquid.

30. The method of any preceding or following embodiment/feature/aspect, further comprising:

activating an ionizing anode pair during the cleaning mode, the ionizing anode pair comprising at least one ionizing anode situated in the dialyzer discharge line upstream of the drain line.

31. The method of any preceding or following embodiment/feature/aspect, wherein the ionizing anode pair comprises a second anode situated in the drain line.

32. The method of any preceding or following embodiment/feature/aspect, wherein the ionizing anode pair comprises a copper anode and a complimentary anode comprising at least one of an aluminum material and a ferrous material, the copper anode and the complimentary anode are situated within the dialyzer discharge line, and the activating comprises supplying an electrical current to the copper anode and to the complimentary anode during the cleaning mode.

33. The method of any preceding or following embodiment/feature/aspect, further comprising activating the ionizing anode pair while generating the ultrasonic waves.

34. The method of any preceding or following embodiment/feature/aspect, further comprising:

pausing the generation of the ultrasonic waves; and activating the ionizing anode pair while the generation of ultrasonic waves is paused.

35. The method of any preceding or following embodiment/feature/aspect, wherein the generating ultrasonic waves creates low pressure volumes of cleaning liquid within the hydraulic system, the generating ultrasonic waves creates high pressure volumes within the cleaning liquid in the hydraulic system, the low-pressure volumes generate gaseous bubbles in the cleaning liquid within the hydraulic system, and the high-pressure volumes rupture the gaseous bubbles in the cleaning liquid within the hydraulic system.

36. The method of any preceding or following embodiment/feature/aspect, wherein the flowing of the cleaning liquid is effected by a dialysate pump, and the method comprises activating the dialysate pump while the ultrasonic generator is activated during the cleaning mode.

37. The method of any preceding or following embodiment/feature/aspect, wherein the flowing of the cleaning liquid is effected by a dialysate pump, and the method comprises deactivating the dialysate pump to pause the flow of the cleaning liquid while the ultrasonic generator is activated.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, a preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A hydraulic system for an extracorporeal blood treatment device comprising:

a dialysate pathway comprising a dialyzer discharge line configured to connect to an outlet of a dialyzer, and a drain line;

at least one pump operationally configured to move a cleaning liquid through the dialysate pathway from the dialyzer discharge line to the drain line;

at least one ultrasonic device configured to generate ultrasonic waves and positioned along the dialysate pathway so as to propagate the ultrasonic waves along at least a portion of the dialysate pathway; and a controller electrically connected to the at least one pump and to the at least one ultrasonic device, wherein the controller is configured to activate the at least one pump to direct a flow of cleaning liquid in the dialysate pathway from the dialyzer discharge line to the drain line, during a cleaning mode, and the controller is further configured to activate the at least one ultrasonic device during the cleaning mode.

2. The hydraulic system for an extracorporeal blood treatment device, of claim 1, wherein the controller is further configured to pause activation of the at least one pump while activating the at least one ultrasonic device, during the cleaning mode.

3. The hydraulic system for an extracorporeal blood treatment device, of claim 1, wherein the dialyzer discharge line comprises a connector end configured to be connected to the outlet of a dialyzer, and the hydraulic system for an extracorporeal blood treatment device further comprises an ionizing anode pair electrically connected to the controller, the ionizing anode pair including at least one ionizing anode situated in the dialyzer discharge line between the connector end and the drain line.

4. The hydraulic system for an extracorporeal blood treatment device, of claim 3, wherein the ionizing anode pair comprises a second anode situated in the drain line.

5. The hydraulic system for an extracorporeal blood treatment device, of claim 3, wherein the ionizing anode pair comprises a copper anode and a complimentary anode comprising at least one of an aluminum material and a ferrous material, wherein the copper anode and the complimentary anode are situated within the dialyzer discharge line and the controller is configured to supply current to the copper anode and to the complimentary anode during the cleaning mode.

6. The hydraulic system for an extracorporeal blood treatment device, of claim 1, further comprising a cleaning liquid within the dialysate pathway, wherein the at least one ultrasonic device is configured to generate ultrasonic waves in the dialysate pathway, to create low pressure volumes of the cleaning liquid in the dialysate pathway, and to create high pressure volumes of the cleaning liquid in the dialysate pathway, the low pressure volumes being of such low pressure as to generate gaseous bubbles, and the high pressure volumes being of such high pressure as to rupture the gaseous bubbles.

7. The hydraulic system for an extracorporeal blood treatment device, of claim 1, wherein the at least one ultrasonic device is configured to propagate ultrasonic waves at a sweep frequency.

8. The hydraulic system for an extracorporeal blood treatment device, of claim 1, wherein the dialyzer discharge line comprises a tubing, the at least one ultrasonic device comprises a collar that surrounds the tubing, and the at least one ultrasonic device propagates ultrasonic waves radially inwardly toward a center of the tubing.

9. The hydraulic system for an extracorporeal blood treatment device, of claim 1, wherein the at least one ultrasonic device further comprises an ultrasonic device coupled to the drain line.

10. The hydraulic system for an extracorporeal blood treatment device, of claim 1, wherein:

the dialysate pathway further comprises a dialyzer feed line configured to connect to an inlet of a dialyzer, and a bypass system;

the controller is also electrically connected to the at least one bypass system;

the bypass system comprises a bypass line fluidly connecting the dialyzer feed line with the dialyzer discharge line;

the bypass system comprises one or more valves configured to be actuated by the controller, during a cleaning mode, to direct a flow of liquid in the dialysate pathway from the dialyzer feed line to the dialyzer discharge line, without passing through a dialyzer; and the controller is configured to operate in preparation for the cleaning mode, by actuating the one or more valves such that liquid in the dialysate pathway is conveyed from the dialyzer feed line, through the bypass line, and into the dialyzer discharge line.

11. The hydraulic system for an extracorporeal blood treatment device, of claim 10, wherein the dialyzer feed line, the dialyzer discharge line, the bypass line, or a combination thereof, comprises a tubing, the at least one ultrasonic device comprises a collar that surrounds the tubing, and the at least one ultrasonic device propagates ultrasonic waves radially inwardly toward a center of the tubing.

12. The hydraulic system for an extracorporeal blood treatment device, of claim 10, wherein:

the dialysate pathway further comprises a balancing device comprising a balancing chamber, a balancing feed line that leads to the balancing chamber and is configured to supply dialysate from a dialysate source into the balancing chamber, and a balancing discharge line that leads away from the balancing chamber and is configured to carry spent dialysate away from the balancing chamber and into the drain line;

the dialyzer feed line extends from the balancing chamber and is configured to supply dialysate from the balancing chamber to a dialyzer during hemodialysis;

the dialyzer discharge line extends to the balancing chamber and is configured to supply spent dialysate from the dialyzer into the balancing chamber during hemodialysis; and the at least one ultrasonic device is configured to generate ultrasonic waves in the balancing chamber during the cleaning mode.

13. The hydraulic system for an extracorporeal blood treatment device, of claim 10, further comprising a dialyzer having a dialyzer inlet and a dialyzer outlet, wherein the dialyzer feed line is connected to the dialyzer inlet, the dialyzer discharge line is connected to the dialyzer outlet, the one or more valves are configured to shut-off the bypass line during a treatment mode so that liquid in the dialysate pathway flows from the dialyzer feed line, into the dialyzer, through the dialyzer, out of the dialyzer outlet, and into the dialyzer discharge line, and the controller is configured to not activate the at least one ultrasonic device during the treatment mode.

14. A method of operating the hydraulic device of claim 1, the hydraulic system comprising the dialyzer discharge line and the drain line, the method comprising:

disconnecting the dialyzer discharge line from a dialyzer;

flowing a cleaning liquid from the dialyzer discharge line to the drain line;

generating ultrasonic waves with an ultrasonic generator disposed along the dialyzer discharge line; and propagating the ultrasonic waves from the dialyzer discharge line toward the drain line during a cleaning mode of operation of the extracorporeal blood treatment device.

15. The method of claim 14, wherein the hydraulic system further comprises a dialyzer feed line and a bypass system, the bypass system comprises a bypass line fluidly connecting the dialyzer feed line with the dialyzer discharge line, the bypass system comprises one or more valves configured to direct a flow of liquid in the hydraulic system from the dialyzer feed line to the dialyzer discharge line, without passing through a dialyzer, and the method further comprises actuating the one or more valves such that liquid in the hydraulic system is conveyed from the dialyzer feed line, through the bypass line, and into the dialyzer discharge line without passing through a dialyzer.

16. The method of claim 15, wherein the hydraulic system further comprises a dialyzer having an inlet and an outlet, the dialyzer feed line is connected to the dialyzer inlet, the dialyzer discharge line is connected to the dialyzer outlet, and the method further comprises:

flowing a dialysate through the dialyzer during a treatment mode, before the actuating of the one or more valves; and then performing the actuating of the one or more valves, during the cleaning mode, after the disconnecting of the dialyzer discharge line from the dialyzer, such that liquid in the hydraulic system is conveyed from the dialyzer feed line, through the bypass line, and into the dialyzer discharge line without passing through the dialyzer.

17. The method of claim 16, wherein during the treatment mode, the dialyzer feed line is supplied with a supply of the dialysate, and during the cleaning mode, the dialyzer feed line is supplied with a cleaning liquid.

18. The method of claim 14, further comprising:

activating an ionizing anode pair during the cleaning mode, the ionizing anode pair comprising at least one ionizing anode situated in the dialyzer discharge line upstream of the drain line.

19. The method of claim 18, wherein:

the generation of the ultrasonic waves is paused; and the ionizing anode pair is activated while the generation of ultrasonic waves is paused.

20. The method of claim 14, wherein the generating ultrasonic waves creates low pressure volumes of cleaning liquid within the hydraulic system, the generating ultrasonic waves creates high pressure volumes within the cleaning liquid in the hydraulic system, the low-pressure volumes generate gaseous bubbles in the cleaning liquid within the hydraulic system, and the high-pressure volumes rupture the gaseous bubbles in the cleaning liquid within the hydraulic system.

* * * * *